(12) United States Patent
Schröder (10) Patent No.: US 7,679,377 B2
(45) Date of Patent: *Mar. 16, 2010

(54) MEASURING APPARATUS AND METHOD FOR DETERMINING A DIELECTRIC PROPERTY, IN PARTICULAR MOISTURE AND/OR DENSITY, IN A PRODUCT

(75) Inventor: Dierk Schröder, Hamburg (DE)

(73) Assignee: Hauni Maschinenbau Ag, Hamburg (DE)

( * ) Notice: Subject to any disclaimer, the term of this patent is extended or adjusted under 35 U.S.C. 154(b) by 91 days.

This patent is subject to a terminal disclaimer.

(21) Appl. No.: 11/793,947

(22) PCT Filed: Dec. 17, 2005

(86) PCT No.: PCT/EP2005/013831

§ 371 (c)(1),
(2), (4) Date: Jun. 22, 2007

(87) PCT Pub. No.: WO2006/069721

PCT Pub. Date: Jul. 6, 2006

(65) Prior Publication Data

US 2008/0164887 A1 Jul. 10, 2008

(30) Foreign Application Priority Data

Dec. 22, 2004 (DE) ........................ 10 2004 063 228

(51) Int. Cl.
*G01R 27/26* (2006.01)
(52) U.S. Cl. ........................ 324/664; 324/637; 324/658; 131/280
(58) Field of Classification Search .................. 324/664
See application file for complete search history.

(56) References Cited

U.S. PATENT DOCUMENTS 3,786,349 A 1/1974 Devenyl 3,979,581 A 9/1976 Reuland et al.
3,996,942 A * 12/1976 Baier ........................ 131/280

(Continued)

FOREIGN PATENT DOCUMENTS

DE 25 00 299 A1 9/1975

(Continued)

OTHER PUBLICATIONS

Caranti G M et al: "A Vector Impedance Meter Digitally Controlled" Review of Scientific Instruments, AIP, Melville, NY, US, vol. 62, No. 12, Dec. 1, 1991, pp. 3092-3097, XP000278580.

(Continued)

*Primary Examiner*—Timothy J Dole
*Assistant Examiner*—Benjamin M Baldridge
(74) *Attorney, Agent, or Firm*—Venable LLP; Robert Kinberg; Kyle D. Petaja (57) ABSTRACT

The application concerns a measuring apparatus for determining a dielectric property, in particular the moisture and/or density, of a product, in particular tobacco, Cotton or some other fibrous product, having a measuring capacitor, a device for generating a high-frequency field in the measuring capacitor, which is influenced by a product which is arranged in a measuring volume of the measuring apparatus, and having a circuit device which includes the measuring capacitor and which is designed to determine suitable measurable variables of the high-frequency field influenced by the product, and is distinquished in that the circuit device is substantially non-resonant at the measuring frequency of the high-frequency field that is used, and measurement is based on the propagation of a travelling high-frequency wave in the measuring capacitor, and the circuit device is designed to determine two mutually independent measurable variables which are dependent on the amplitude and phase of the high-frequency wave influenced by the product. The application further concerns a corresponding measuring method.

26 Claims, 6 Drawing Sheets

U.S. PATENT DOCUMENTS

| | | | |
|---|---|---|---|
| 4,114,090 A | | 9/1978 | Poskitt |
| 4,505,186 A | * | 3/1985 | Meier et al. ............... 92/5 R |
| 4,947,131 A | * | 8/1990 | Mayer et al. ............... 324/671 |
| 5,208,544 A | | 5/1993 | McBrearty et al. |
| 5,302,907 A | * | 4/1994 | Hohenstein et al. ......... 324/655 |
| 6,073,480 A | * | 6/2000 | Gokhfeld ................... 73/29.02 |
| 6,346,819 B1 | * | 2/2002 | Joss et al. .................. 324/665 |
| 6,768,317 B2 | * | 7/2004 | Moller et al. ............... 324/637 |
| 2003/0020494 A1 | * | 1/2003 | Desmier et al. ............. 324/667 |
| 2003/0107729 A1 | | 6/2003 | Furter |
| 2008/0084220 A1 | * | 4/2008 | Schroder .................... 324/658 |

FOREIGN PATENT DOCUMENTS

| | | |
|---|---|---|
| DE | 24 41 832 A1 | 3/1976 |
| DE | 27 00 972 | 7/1978 |
| DE | 27 00 972 C3 | 6/1980 |
| DE | 37 43 216 A1 | 6/1989 |
| DE | 38 25 111 A1 | 1/1990 |
| DE | 196 51 355 | 6/1998 |
| DE | 100 37 180 | 1/2002 |
| DE | 101 00 664 A1 | 7/2002 |
| EP | 902 277 A1 | 7/1998 |
| EP | 924513 A1 | 6/1999 |
| EP | 1 327 876 B1 | 7/2003 |
| EP | 1 330 961 A1 | 7/2003 |
| FR | 1315918 | 1/1963 |
| GB | 717127 | 10/1954 |
| GB | 1132763 A | 11/1968 |

OTHER PUBLICATIONS

Smit Q et al: "General purpose self-tuning capacitance sensor [for oil] recycling and soil moisture measurement application]" IMTC/98 Conference Proceedings. IEEE Instrumentation and Measurement Technology Conference. Where Instrumentation is Going (CAT. No. 98CH36222) IEEE New York, NY, USA, vol. 2, 1998, pp. 1074-1078 vol., XP010281750.

Huang S M et al: "Electronic transducers for industrial measurement of low value capacitances" Journal of Physics E (Scientific Instruments) vol. 21, No. 3, Mar. 1988, pp. 242-250.

Iacopini E et al: "Digital techniques applied to phase-sensitive detection" Journal of Physics E (Scientific Instruments) vol. 16, No. 9, Sep. 1983, pp. 844-847, XP020017183.

Saniie J et al: "Digital phase detection based on in-phase and quadrature sampling" Journal of Physics E. Scientific Instruments, IOP Publishing, Bristol, vol. 16, No. 7, Jul. 1, 1983 pp. 606-607, XP020017126.

International Search Report dated Jul. 19, 2006, issued in PCT/EP2005/013831.

International Search Report dated Jun. 13, 2006, issued in PCT/EP2005/013830.

German Patent and Trademark Office Examination Report dated Oct. 19, 2005, issued in DE 10 2004 063 229.4.

Non Final Office Action issued in U.S. Appl. No. 11/793,948 on Feb. 26, 2009.

* cited by examiner

MEASURING APPARATUS AND METHOD FOR DETERMINING A DIELECTRIC PROPERTY, IN PARTICULAR MOISTURE AND/OR DENSITY, IN A PRODUCT

The invention concerns a measuring apparatus for determining a dielectric property, in particular the moisture and/or density, of a product, in particular tobacco, cotton or some other fibrous product, according to the preamble of claim 1. The invention further concerns a corresponding measuring method.

To determine a dielectric property of a material, the use of microwave measuring apparatuses is known from EP 0 902 277 A1, for example. On account of the necessary high precision of measurement and the high frequencies used, the circuitry is highly elaborate.

In the high-frequency range at lower frequencies, capacitive measuring apparatuses are known for determining the moisture or mass of tobacco, in which a measuring capacitor and a coil as frequency-determining parts are connected in a high-frequency oscillating circuit (U.S. Pat. No. 3,979,581, DE 25 00 299, DE 24 41 832, DE 37 43 216 C2, DE 38 25 111 A1). The measurable variables determined are, for example, the resonant frequency and resonant amplitude of the high-frequency field, which are affected by the product. The temperature dependence of the capacitor and coil has an effect on the precision of measurement. Special, particularly temperature-stable capacitors and coils such as are known for example from DE 37 43 216 C2 are elaborate and expensive. Also, the use of a high capacitance and high inductance can be necessary to generate the measuring resonant frequency used, leading to an increase in manufacturing costs and the size of measuring capacitor and coil.

Capacitive high-frequency measuring apparatuses are also known for determining the moisture or mass of a material, in which a measuring capacitor is supplied with two high-frequency waves of different frequency, and the amplitudes of the two frequency components influenced by the product are determined as measurable variables. The generation of two high-frequency waves with different frequencies is associated with increased expenditure.

It is the object of the present invention to provide a structurally simple and compact high-frequency measuring apparatus with high precision of measurement and improved stability to temperature effects.

The invention achieves this object with the features of claims 1 and 26. By using a travelling high-frequency wave and a substantially non-resonant circuit device, in which the measuring capacitor is therefore not a frequency-determining part of a measuring oscillating circuit, the use of an oscillating circuit coil which is sensitive to temperature effects can be dispensed with. "Substantially" means that resonant field components are not excluded as long as the principle of measurement is essentially based on a progressive wave. As no condition of resonance for a measuring oscillating circuit has to be fulfilled, the measuring capacitor can have a lower capacitance than in the state of the art, preferably less than 10 pF, which reduces the elaborateness and size. To enable density compensation particularly when determining the moisture and/or moisture compensation when determining the density, the measurement of two independent measurable variables is provided. According to the invention, in this case two measurable variables dependent on the amplitude and phase of the high-frequency wave are determined. Basically, therefore, the generation of a high-frequency wave is sufficient, which reduces the elaborateness compared with those apparatuses which are based on the use of several high-frequency waves with different high frequencies.

The term "high frequency" basically means, as differentiated from the microwave range, fields with a frequency below 100 MHz. As a rule the frequency is more than 10 kHz, preferably more than 100 kHz. More preferably the frequency is at least 1 MHz, and in particular for tobacco more preferably at least 5 MHz, since towards lower frequencies an accurate enough measurement is possible only within an increasingly limited measuring range.

The part of the circuit device which serves to determine the measurable variables is as a rule connected to the output of the actual measuring circuit which includes the measuring capacitor. While the measuring circuit as a rule comprises one output for the high-frequency wave influenced by the product, the circuit for determining the measurable variables as a rule comprises two outputs for the given measurable variables. It is also possible for the measuring circuit and the circuit for determining the measurable variables to form a unit. The circuit for determining the measurable variables is connected to the input of the actual evaluating device for determining the dielectric property of the product. It is also possible for the circuit for determining the measurable variables and the evaluating device to form a unit.

In a preferred embodiment, the part of the circuit device which serves to determine the measurable variables is constructed with digital electronics. This allows the use of simple methods to determine the desired measurable variables, for example, the capacitive fraction and the loss fraction of the output voltage value of the measuring circuit. A particularly simple and therefore preferred method is based on the orthogonality of the sine and cosine fractions and includes the measurement of a discrete number of n measured values, for example, voltage values, over each oscillation period of the high-frequency field, separate multiplication of the n measured values by corresponding sine and cosine values, and separate addition of these sine and cosine products. The totals obtained constitute the measurable variables or can be further processed to determine the measurable variables.

A particularly simple form of a measuring circuit, i.e. part of the circuit device including the measuring capacitor, is an RC network, preferably with an operational amplifier. This preferably involves an RC differentiating network, but an RC integrating network may also be used, for example.

In a preferred embodiment, parts of the sensor are made of a material with a low temperature expansion coefficient in order to keep the effects of temperature fluctuations on the precision of measurement as low as possible. For the same purpose the sensor can have an additional device for keeping the temperature of the measuring capacitor constant. An additional device for measuring the temperature of the measuring capacitor, for example, a temperature sensor, is also conceivable in order to be able to correct the measuring signal accordingly.

Preferably the capacitor is arranged essentially perpendicular to the direction of transport of the product. With a plate capacitor, therefore, the capacitor plates are arranged perpendicular to the direction of transport. This makes it possible to arrange the electrodes a short distance from each other, for example, less than the thickness of the endless product rod. This can result in improved resolution when measuring the product profile in the longitudinal direction.

The sensor is designed to feed the product through the space formed between the electrodes of the measuring capacitor, to allow detection of the product as completely and uniformly as possible. A leakage field sensor is therefore preferably not involved.

Another preferred embodiment concerns the measurement of a relatively broad product, for example, a tobacco or tow web or a cotton fleece, or a plurality of endless product rods located beside each other. In this case the sensor includes a plurality of measuring capacitors arranged across the width of the product. This arrangement permits the measurement of a product profile across the width of the product in a simple manner. The electrodes supplied with the high-frequency wave are kept at the same potential, for example, simply short-circuited, to minimize crosstalk between the measuring capacitors. For the same purpose the other electrodes are preferably also in each case kept virtually at the same potential by means of inverting operational amplifiers.

Further advantageous features are apparent from the subsidiary claims and the description of advantageous embodiments with reference to the attached drawings. They show:

The capacitive measuring apparatus 10 according to FIGS. 1 to 6 includes a high frequency generating device 13 for generating a high-frequency wave which is supplied via an input wire 14 to a circuit device 28. The circuit device 28 includes a measuring capacitor 11 through which is passed the product 12 to be measured, which is in the form of an endless rod in the present case. The high-frequency wave generated by the high frequency generating device 13 is passed to an electrode 15 of the measuring capacitor 11 in order to generate in it a high-frequency field which interacts with the product 12. The high-frequency wave emanating from the other electrode 16 of the measuring capacitor 11 and influenced by the product 12 in the measuring capacitor 11 is processed by means of the circuit device 28 in order to determine two measurable variables independent of each other and dependent on the amplitude and phase of the high-frequency wave influenced by the product 12. These are preferably two measurable variables dependent on the capacitance and the dielectric loss factor of the measuring capacitor 11. Measuring signals corresponding to the measurable variables are passed to the evaluating device 21, for example, a suitably programmed computer, by means of which the desired dielectric property, for example, the moisture and/or density, of the product 12 is determined from the given measurable variables. On the basis of evaluation of two measurable variables independent of each other, it is possible here for example to determine a product density which is independent of the product moisture and/or a product moisture which is independent of the product density. For evaluation, calibration curves stored in the evaluating device 21 and predetermined by calibration can be used.

Figure 1:
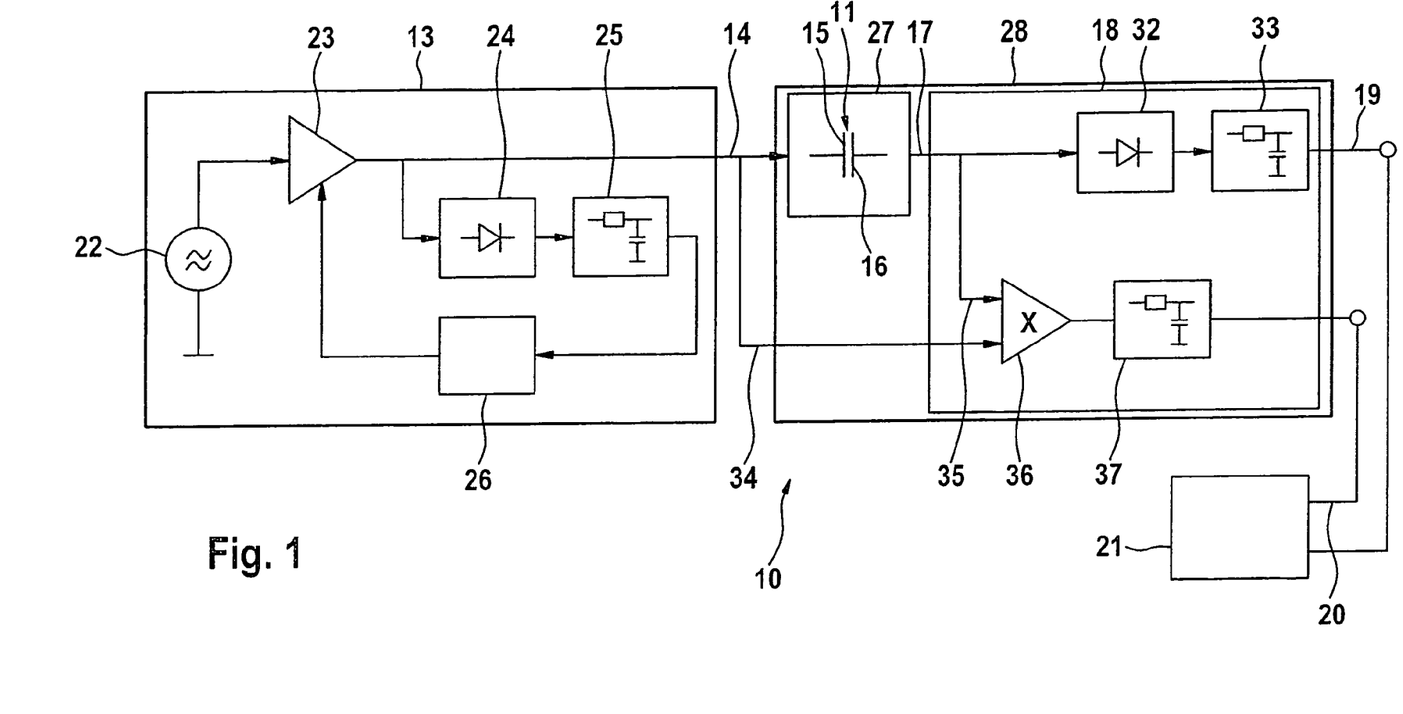
FIG. 1: a schematic circuit of an essentially analogue measuring apparatus.

The embodiment according to FIG. 1 concerns an essentially analogue measuring apparatus. The high frequency generating device 13 includes a harmonic oscillator 22 for generating a high-frequency wave. The voltage amplitude $U_e$ of the generated high-frequency wave is preferably kept constant by means of a regulating device 23-26 in order to allow measurement uninfluenced by fluctuations of input amplitude. For this purpose the high-frequency wave generated by the harmonic oscillator 22 is supplied to a controllable amplifier 23. The output signal of the amplifier 23 is supplied to a rectifier 24 whose output signal is passed on via the low-pass filter 25 to a controller 26. The controller 26 controls the amplifier 23 in such a way that the amplitude $U_e$ of the harmonic oscillation at the output of the amplifier 23 has a constant value.

Figure 2:
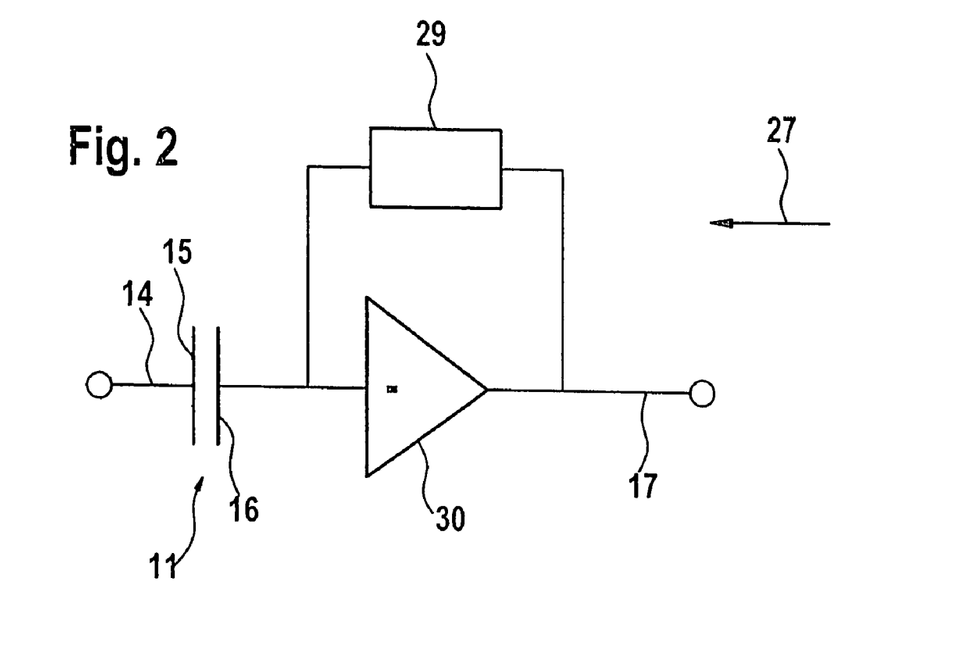
FIG. 2: a differentiating measuring circuit for a measuring apparatus.
Figure 3:
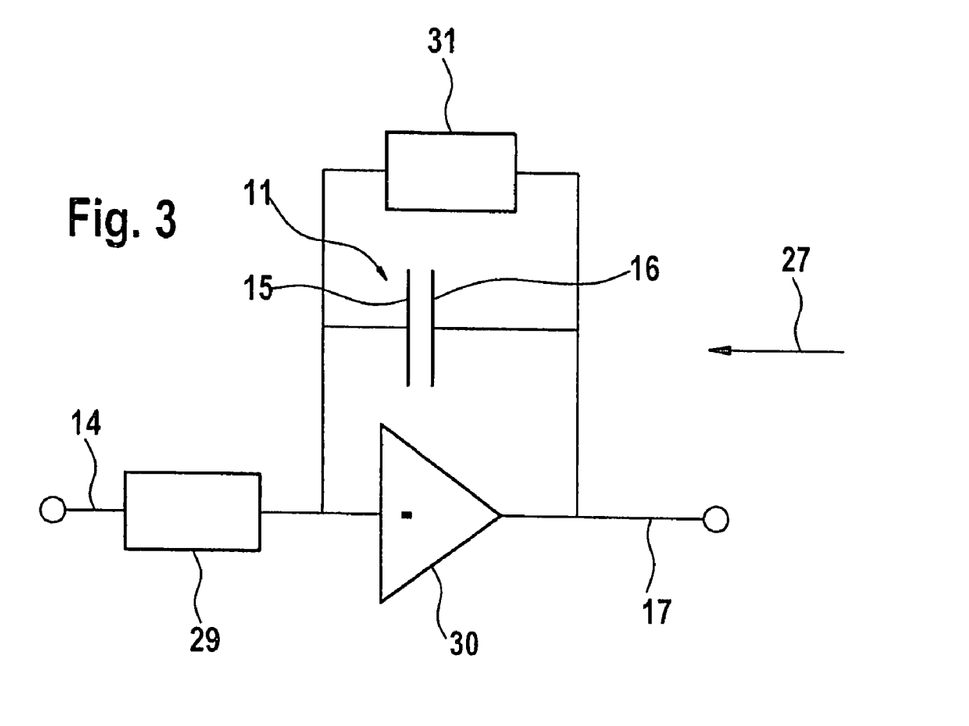
FIG. 3: an integrating measuring circuit for a measuring apparatus.

The measuring circuit 27 is the part of the circuit device 28 directly connected to the measuring capacitor 11. Any measuring circuit which is designed to generate an adequate amplitude and phase variation of the high-frequency wave as a result of the product 12 passing through the measuring capacitor 11 is suitable here. Two preferred embodiments of the measuring circuit 27 are shown in FIGS. 2 and 3, wherein the measuring capacitor 11, a resistor 29 and an inverting operational amplifier 30 are connected in a differentiating arrangement according to FIG. 2 or an integrating arrangement according to FIG. 3. The non-inverting input of the operational amplifier 30 is appropriately grounded. With the integrating arrangement according to FIG. 3, an additional resistor 31 is provided to prevent, if necessary, the output signal from passing to the boundary (e.g., to prevent the output of the operational amplifier 30 from saturating). The output signal of the measuring circuit 27 which corresponds to the outgoing high-frequency wave exhibits, due to interaction with the product 12, a voltage amplitude $U_a$ which is altered from the input amplitude $U_e$, as well as a phase shift of δ compared with the input signal.

The high-frequency wave influenced by the product 12 is passed via the output wire 17 of the measuring circuit 27 to the device 18 for determining the measurable variables. The device 18 for determining the measurable variables determines suitable measurable variables from the modified high-frequency signal. For this purpose, in the embodiment according to FIG. 1 the output signal of the measuring circuit 27 is delivered to a rectifier 32 and smoothed in a low-pass filter 33. The signal obtained in this way is proportional to the output amplitude $U_a$. Furthermore, the input signal generated by the high frequency generating device 13 is delivered via the wire 34 to the device 18 for determining the measurable variables. In general, advantageously a signal dependent on the high-frequency wave generated is passed to the circuit device 28 via a wire 34, 234 provided in addition to the measuring wire via the measuring capacitor 11, in order to be able to use the phase information of the input signal for determining the phase shift of the output signal. In the present case the input signal of the measuring capacitor 11 is passed via the wire 34 and the output signal of the measuring capacitor 11 or the measuring circuit 27 is passed via a wire 35 to the multiplication amplifier 36, in which they are multiplied by each other and smoothed with a low-pass filter 37. The signal obtained in this way is proportional to the output amplitude $U_a$ times the sine (or cosine) of the phase shift δ. The measurable variables determined by means of the device 18 for determining the measurable variables are correlated in a defined manner with the real and imaginary parts of the dielectric constants, or with the moisture and density of the product 12. For corresponding evaluation, the given measuring signals are passed via the output wires 19, 20 to the evaluating device 21 in which evaluation is carried out by means of a computer program stored therein, for example.

Figure 4:
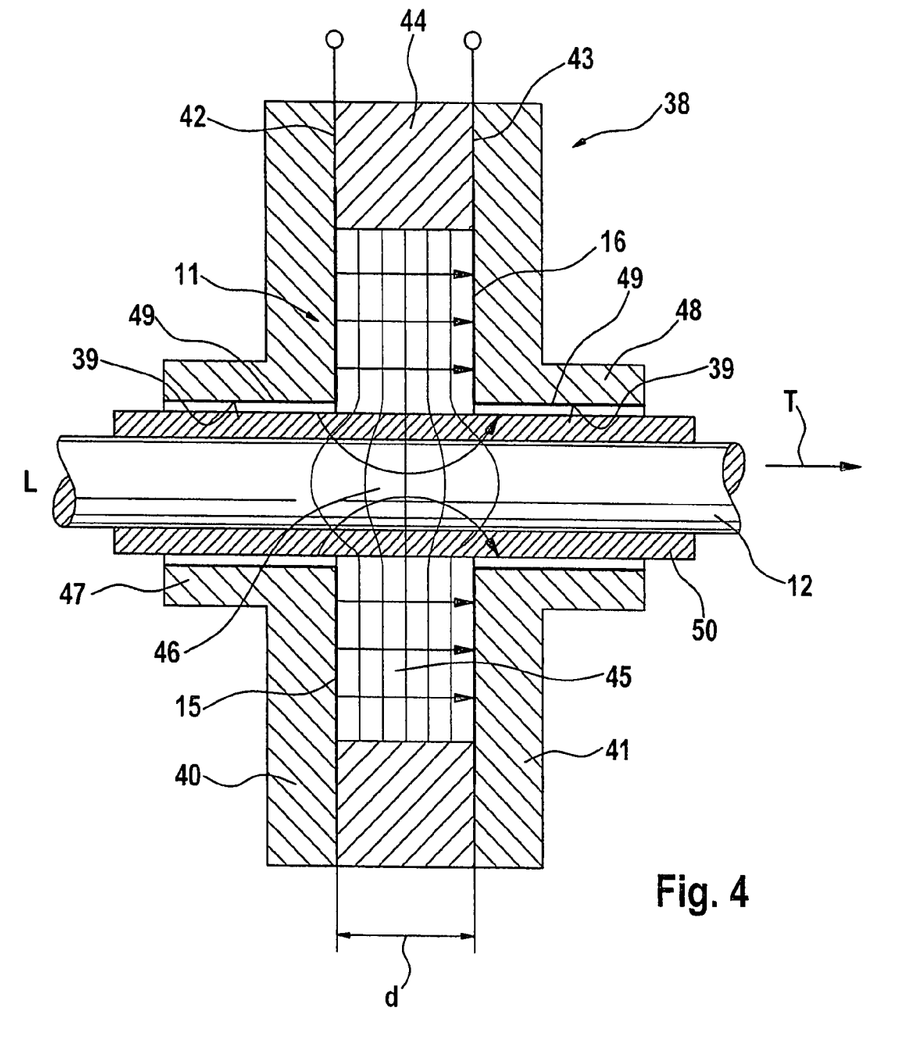
FIG. 4: a longitudinal sectional view of a capacitive sensor.

A preferred embodiment of a high-frequency sensor 38 is shown in FIG. 4. The sensor 38 is constructed substantially rotationally symmetrically about the longitudinal axis L.

Through a central longitudinal bore 39 of the sensor 38 the endless product rod 12, for example, an endless tobacco rod, is passed in the direction of transport T which coincides with the longitudinal direction L. The sensor includes two rotationally symmetrical, disc-shaped base bodies 40, 41 which are oriented perpendicularly to the longitudinal direction L and which are spaced apart from each other by means of an outer, annular, non-conductive boundary body 44 and which each comprise a central through-hole 39 for the endless product rod. To each of the inner surfaces of the base bodies 40, 41 oriented perpendicularly to the longitudinal direction L is applied an electrode 15, 16 of the measuring capacitor 11 in the form of a metal surface, for example a metal coating, for example by vapor deposition of gold. The measuring capacitor 11 is therefore designed as a plate capacitor with plate-like electrodes 15, 16 which are disc-shaped and oriented perpendicularly to the longitudinal direction L and comprise a central through-hole for the endless product rod 12. In this arrangement the field lines run substantially parallel to the direction of transport. Between the base bodies 40, 41 is formed a field-filled space 45 which is radially outwardly closed off by the boundary body 44. The high-frequency field extends into the central product space 46 and there interacts with the product 12. The plates 15, 16 have a shorter radius than the base bodies 40, 41 in order to prevent emergence of the high-frequency field into the environment of the sensor. The plates 15, 16 of the plate capacitor 11 can be arranged a short distance d from each other to improve the measuring resolution in the longitudinal direction and allow accurate measurement of the product profile in the longitudinal direction. The distance d can be in particular shorter than the diameter of the endless product rod 12 and, for example, less than 8 mm, preferably less than 4 mm. Conductive connections 42, 43 between the electrodes 15, 16 and external electrical terminals are also provided. The base bodies 40, 41 each have a tubular, axially outwardly extending extension 47, 48 encompassing the endless product rod. The extensions 47, 48 have a metal surface or coating on the inner wall, which is appropriately connected to the electrodes 15, 16. The metal coating 49 forms a metal chimney to prevent leaking of the field from the product through-holes of the capacitor 11. Furthermore, a tube 50 of non-conductive material directly surrounding and guiding the endless product rod 12 and extending over the whole length of the sensor is provided, which prevents contamination of the interior of the sensor by product residues. In a further embodiment the field-filled space 45 formed between the electrodes 15, 16 can be partially or completely filled with a dielectric material, apart from the product space, for positively influencing the field pattern.

The bodies 40, 41, 44 of the sensor 38 are preferably made of a non-conductive material with a very low temperature expansion coefficient, for example, Zerodur, in order to achieve increased dimensional stability of the sensor 38 to temperature effects. On account of the reduced dependence of the capacitance properties of the measuring capacitor 11 on the ambient temperature, improved precision of measurement can be achieved. For the same purpose, preferably a regulating device, not shown, is provided for keeping the sensor temperature constant. It is also conceivable that the base bodies 40, 41 of the sensor 38 are partially or completely made of metal.

Figure 5:
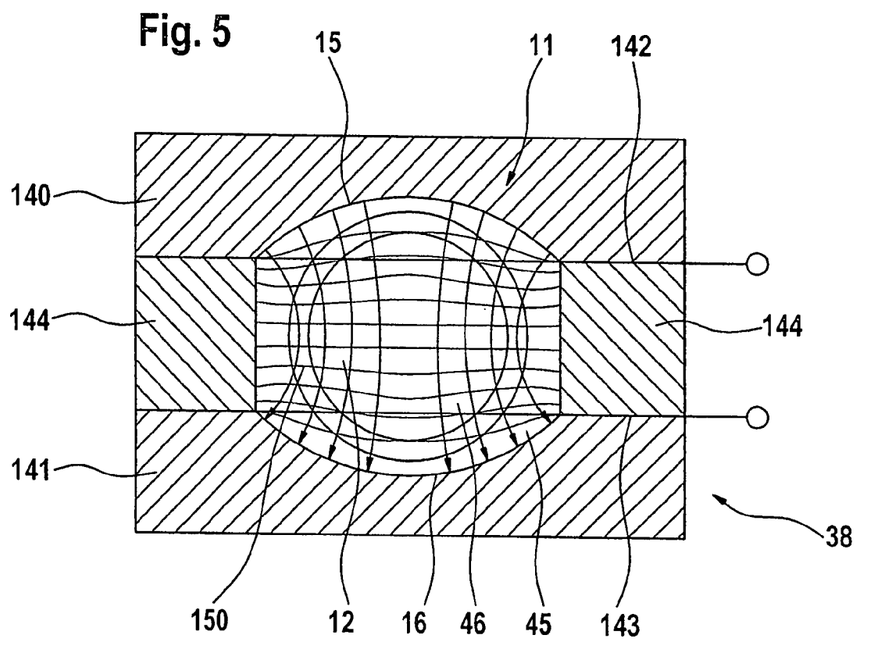
FIG. 5: a cross-sectional view of a capacitive sensor in a further embodiment.

Another embodiment of a sensor 38 is shown in FIG. 5, parts corresponding to each other being denoted by corresponding reference numbers in the 100s. The electrodes 15, 16 are formed by plates which are arranged parallel to the direction of transport which is oriented perpendicularly to the plane of the paper. The field lines run in this example substantially perpendicularly to the direction of transport. The plates 15, 16 are preferably arranged round the endless product rod 12 and for this purpose are preferably curved.

Figure 6:
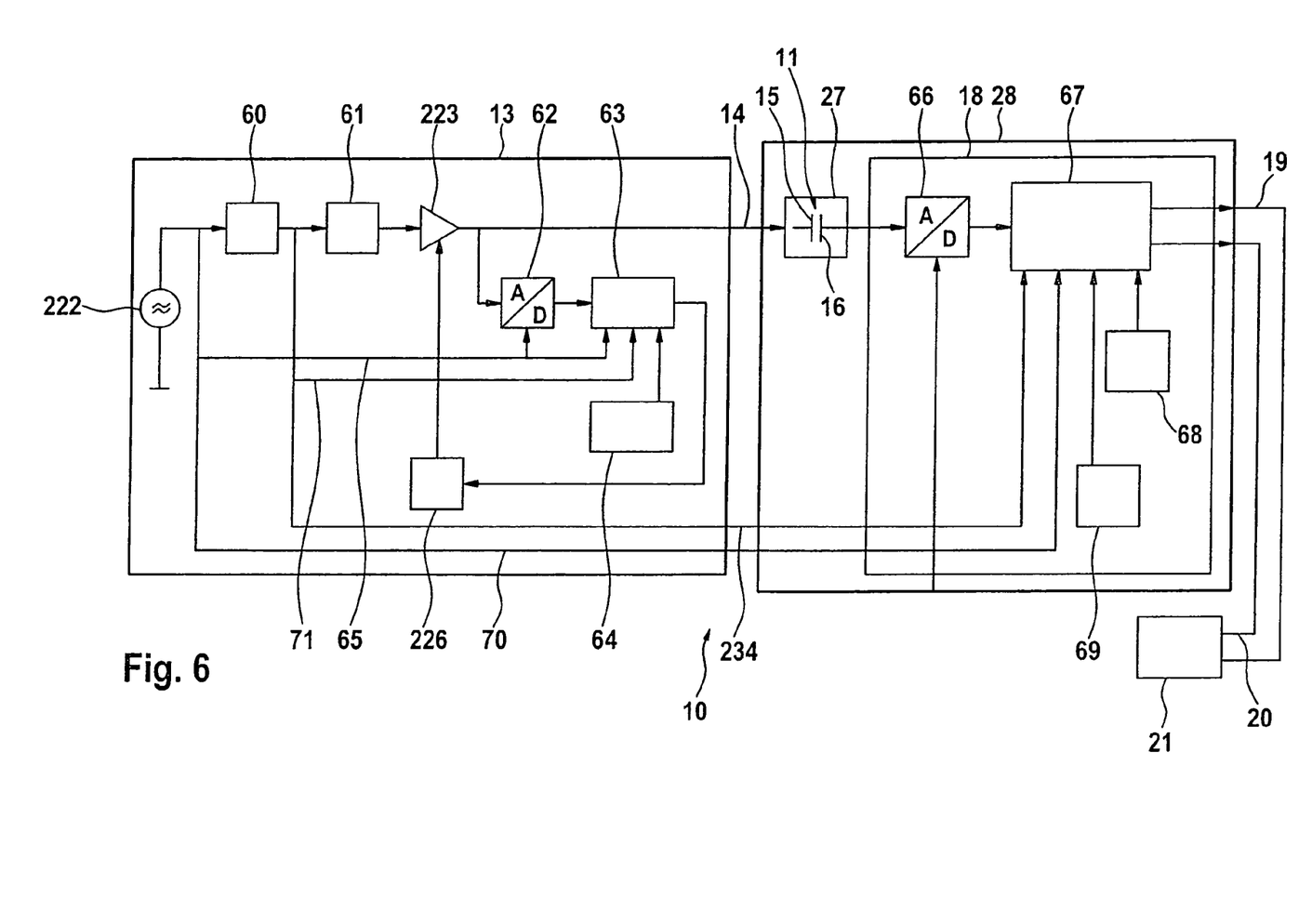
FIG. 6: a schematic circuit of an essentially digital measuring apparatus.

A preferred embodiment of a measuring apparatus 10 is shown in FIG. 6, parts corresponding to each other being denoted by corresponding reference numbers in the 200s. Unlike the embodiment according to FIG. 1, in particular the device 18 for determining the measurable variables is constructed with digital electronics. For this purpose the device 18 for determining the measurable variables has an A/D converter 66 to which is passed the measuring signal emitted by the measuring circuit 27. The A/D converter 66 is clock-controlled with a scanning frequency which is higher by a factor of n than the frequency of the high-frequency wave, n being a natural number greater than 1. The clock signal for the A/D converter 66 is generated by means of the quartz oscillator 222 in the form of a square-wave signal with a frequency of for example 50 MHz, so that in the present example n=10. In general, therefore, the measuring apparatus 10 has a device 222 for generating a scanning signal with a scanning frequency which is higher by a factor of n than the frequency of the high-frequency wave. The scanning signal is passed via the wire 70 to the A/D converter 66.

The measured values scanned with the A/D converter 66 are passed to the digital processing device 67 which is programmed to determine suitable measurable variables independent of each other. In a preferred method for determining the measurable variables, each scanned measurement is multiplied on the one hand by the corresponding value of sine function and on the other hand by the corresponding value of cosine function. For this purpose the scanning signal is passed via the wire 70 to the processing device 67. The sine and cosine values can for example be taken from corresponding tabular memories 68, 69. The n sine values and n cosine values obtained in this way are then added up separately over a period of the high-frequency field, so that two totals are obtained. For this purpose the high-frequency input signal is passed via the wire 234 to the processing device 67, so that the latter works in phase with the high frequency generating device 13. From the totals obtained can be clearly determined, on the basis of given orthogonality relationships, the two desired measurable variables dependent on the amplitude and phase of the measuring signal influenced by the product 12. For corresponding evaluation, the given measuring signals are passed via the output wires 19, 20 to the evaluating device 21 in which evaluation is carried out for example by means of a computer program stored therein.

Advantageously, the signal generated by the high-frequency source 222 can also be used to generate the high-frequency wave used for measurement. For this purpose the signal generated by the high-frequency source 222 is divided by means of the divider stage 60 by a factor of n down to a square wave of synchronous phase having a measuring frequency of 5 MHz in the present case, and then converted with the PLL circuit 61 to a sinusoidal signal of synchronous phase with the same frequency.

The control device 223, 62-64, 226 for keeping constant the voltage amplitude $U_e$ of the high-frequency wave emitted by the amplifier 223 can also be constructed with digital electronics. In this case the output signal of the amplifier 223 is supplied to an A/D converter 62 which is controlled via a wire 65 with the scanning signal of 50 MHz, as a result of which n scanned values of the signal emitted by the amplifier 223 are generated to each period. The measured values scanned with the A/D converter 62 are passed to the digital processing device 63. With a preferred method, each scanned voltage value is multiplied by the corresponding value of cosine function. For this purpose the scanning signal is passed via the wire 65 to the processing device 63. The cosine values can for example be taken from a corresponding tabular memory 64. The n cosine values obtained in this way are then added up over a period of the high-frequency field. For this purpose the high-frequency input signal is passed via a wire 71 to the processing device 63, so that the latter works in phase with the high frequency generating device 13. The output signal of the processing device 63 is forwarded to the controller 226 which controls the amplifier 223 in such a way that the output signal of the processing device 63 and hence the amplitude $U_e$ of the oscillation at the output of the amplifier 223 has a constant value.

Figure 7:
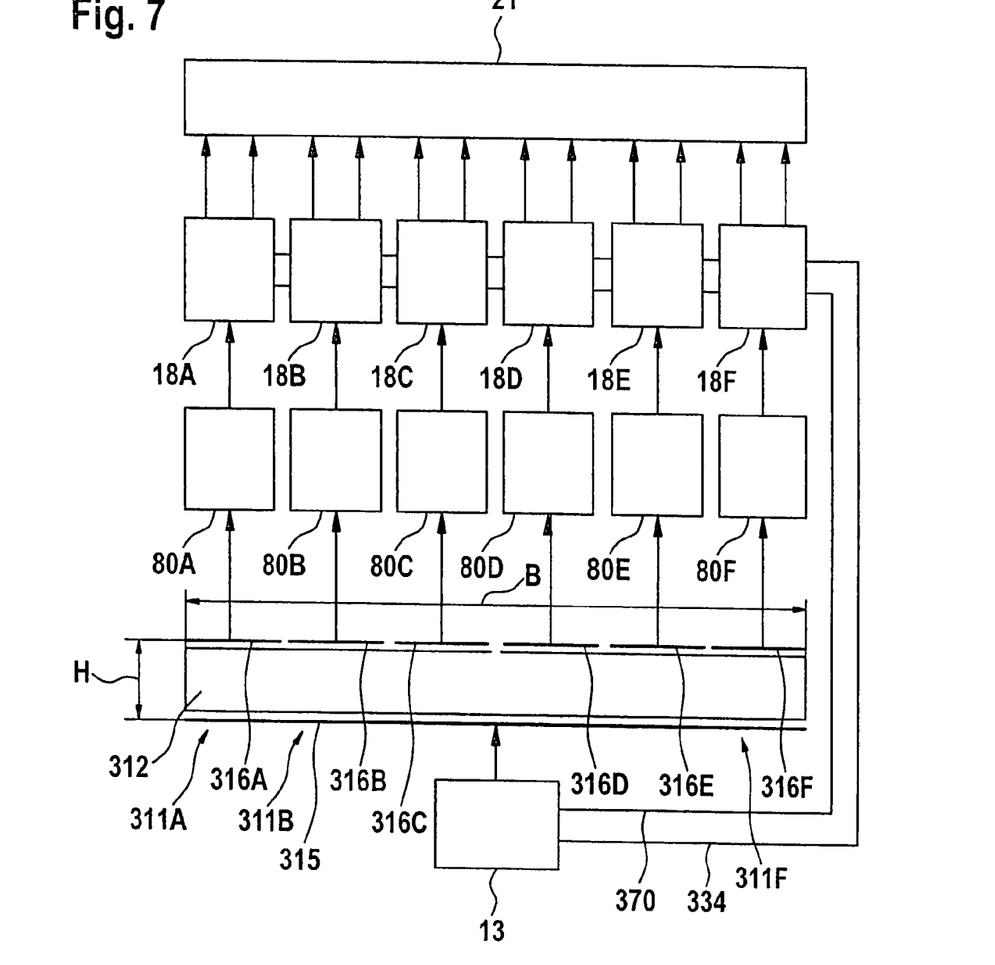
FIG. 7: a schematic circuit of a measuring apparatus for measurement on a wide product.
Figure 8:
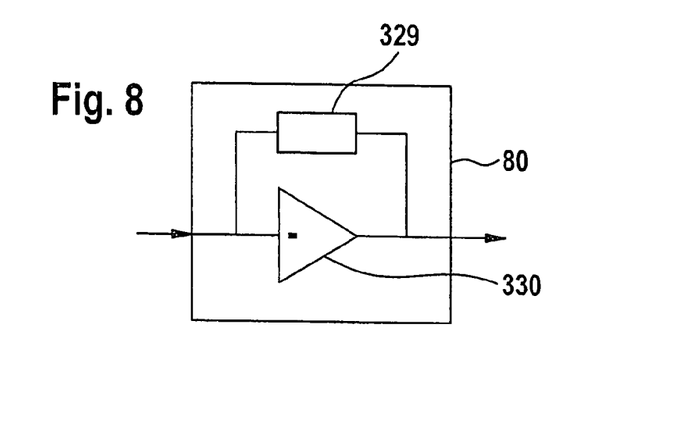
FIG. 8: an operational amplifier for a differentiating measuring circuit for the measuring apparatus from FIG. 7.

The embodiment according to FIG. 7 serves in particular for measurement on a wide, web-like product 312, for example, a tobacco web, a tow web or a cotton fleece, whose width B is substantially greater, for example at least by a factor of 3, than its height H. Another application concerns measurement on a plurality of endless product rods located adjacent to each other, for example, endless tobacco rods. The direction of transport runs perpendicularly to the plane of the paper. Parts corresponding to each other are denoted by corresponding reference numbers in the 300s. In this embodiment a plurality of measuring capacitors 311A, 311B, . . . are used, here six for example, which are arranged across the width of the product. This arrangement allows the measurement of a profile, for example, the density profile, across the width of the product. The measuring capacitors 311A, 311B, . . . are appropriately supplied by the same high frequency generating device 13. Preferably, all the input electrodes 315 of the measuring capacitors 311A, 311B, . . . are at the same potential, at its simplest by short-circuiting the electrodes, as shown in FIG. 7. This minimizes crosstalk between the measuring capacitors 311A, 311B, . . . . The output electrode 316A, 316B, . . . of each measuring capacitor 311A, 311B, . . . is connected to a measuring circuit 80A, 80B, . . . . The measuring circuit 80A, 80B, . . . is preferably constructed as shown in FIG. 8 and then forms, together with the respective measuring capacitor 311A, 311B, . . . , a differentiating measuring circuit 27 as shown in FIG. 2. The use of one inverting operational amplifier 330 each, connected to the output of the measuring capacitor 311A, 311B, . . . is particularly advantageous in this embodiment, because as a result thereof, the output electrodes 316A, 316B, . . . of all the measuring capacitors 311A, 311B, . . . are virtually at the same potential, particularly grounded. This minimizes crosstalk between the measuring capacitors 311A, 311B, . . . . The output of each measuring circuit 80A, 80B, . . . is appropriately connected to a device 18A, 18B, . . . for determining the measurable variables, which can be constructed in particular with digital electronics, for example, as shown in FIG. 6. The devices 18A, 18B, . . . for determining the measurable variables are appropriately connected to the evaluating device 21. The corresponding methods for determining the measurable variables and the dielectric quantities are preferably carried out as described above.

The invention claimed is:

1. Measuring apparatus for determining at least one dielectric property of a tobacco, cotton or other fibrous product, comprising:
   a device for generating a first high frequency wave;
   a measuring volume in which a product may be arranged; and
   a circuit device comprising:
   a measuring capacitor including first and second electrodes and a measuring volume located between the electrodes, wherein the first high frequency wave is applied to one of the electrodes to generate a high frequency field in the measuring capacitor influenced by a product arranged in the measuring volume of the measuring apparatus, wherein a second high frequency wave is produced at the other of the electrodes in dependence on the high frequency field; and
   a measuring device having an input coupled to the second high frequency wave to measuring variables of the second high frequency wave, wherein the circuit device is substantially non-resonant at the frequency of the high frequency field, the variables are based on the propagation of the second high-frequency wave, the measuring device operates to determine two mutually independent measurable variables which are dependent on the amplitude and phase of the second high-frequency wave, and the measuring device including a digital processing device, the measuring device samples the second high frequency wave with a sampling frequency higher than the frequency of the second high frequency wave by a factor of n, wherein n is a positive integer, and the digital processing device separately multiplies n sampled measurements over a period of the second high frequency wave by corresponding sine and cosine values and separately adds up the sine and cosine products.

2. Measuring apparatus according to claim 1, further comprising a sensor encompassing the measuring capacitor, the sensor comprising a material with a low temperature expansion coefficient.

3. Measuring apparatus according to claim 1, further comprising a sensor encompassing the measuring capacitor, the sensor comprising a device for keeping the temperature of the measuring capacitor constant.

4. Measuring apparatus according to claim 1, wherein the measuring capacitor is arranged substantially perpendicularly to a direction of transport of the product.

5. Measuring apparatus according to claim 1, further comprising a sensor encompassing the measuring capacitor, wherein the measuring capacitor includes electrodes, and wherein the sensor is operative to feed the product through the space formed between the electrodes of the measuring capacitor.

6. Measuring apparatus according to claim 1, wherein the measuring capacitor includes electrodes, and wherein each electrode has a central product feedthrough opening.

7. Measuring apparatus according to claim 6, further comprising a tubular, outwardly extending conducting surface located on each electrodes, wherein the conducting surfaces surround the product.

8. Measuring apparatus according to claim 1, wherein the measuring capacitor comprises eletrodes formed by a metal coating.

9. Measuring apparatus according to claim 1, further comprising a sensor encompassing the measuring capacitor, wherein the sensor comprises a non-conducting portion for defining a field-filled space of the measuring capacitor.

10. Measuring apparatus according to claim1, further comprising a sensor encompassing the measuring capacitor, wherein the sensor has a non-conducting tube directly surrounding the product.

11. Measuring apparatus according to claim 1, wherein the measuring capacitor includes electrodes defining a field filled space, and the field filled space is partially or completely filled with a dielectric material.

12. Measuring apparatus according to claim 1, wherein the circuit device is operative to determine a measurable variable dependent on the capacitance of the measuring capacitor.

13. Measuring apparatus according to claim 1, wherein the circuit device is operative to determine a measurable variable dependent on the loss factor of the measuring capacitor.

14. Measuring apparatus according to claim 1, wherein the circuit device is operative to determine the phase shift of the high-frequency wave influenced by the product.

15. Measuring apparatus according to claim 1, wherein the measuring capacitor forms part of an RC network.

16. Measuring apparatus according to claim 1, wherein the circuit device further comprises an operational amplifier.

17. Measuring apparatus according to claim 1, wherein the frequency of the high-frequency wave is below 100 MHz.

18. Measuring apparatus according to claim 1, wherein the frequency of the high-frequency wave is greater than 100 KHz.

19. Measuring apparatus according to claim 1, wherein the capacitance of the measuring capacitor is less than 10 pF.

20. Measuring apparatus according to claim 1, wherein the device for generating a high-frquency wave has a control device for keeping the amplitude of the high-frequency wave constant.

21. Measuring apparatus according to claim 1, wherein the measuring apparatus includes a plurality of measuring capacitors arranged lengthwise across the product.

22. Measuring apparatus according to claim 1, wherein the measuring capacitors include electrodes supplied with the high-frequency wave, wherein the electrodes are kept at the same potential.

23. Measuring apparatus according to claim 1, wherein the measuring capacitors include electrodes supplied with the high-frequency wave and kept virtually at the same potential by means of at least one inverting operational amplifier.

24. Measuring apparatus according to claim 1, wherein the measuring capacitors include electrodes connected to the circuit device for determining suitable measure variables of the high-frequency wave influenced by the product.

25. Measuring apparatus according to claim 1, wherein the frequency of the high-frequency wave is above 5 MHz.

26. Measuring method for determining at least one dielectric property,of a tobacco, cotton or other fibrous product, comprising:
- placing the product in a measuring volume located between electrodes of a measuring capacitor;
- generating a first high frequency wave;
- inputting the first high frequency wave into a non-resonant circuit device, the circuit device comprising the measuring capacitor;
- generating a high frequency field that is influenced by the product arranged in the measuring volume by applying the first high frequency wave to one of the electrodes of the measuring capacitor;
- producing a second high frequency wave at the other electrode of the measuring capacitor in dependence on the high frequency field;
- measuring variables of the second high-frequency wave;
- determining two mutually independent variables, wherein the two variables are dependent on the amplitude and phase of the second high-frequency wave;
- sampling the second high-frequency wave with a sampling frequency higher than the frequency of the second high frequency wave by a factor of n, wherein n is a positive integer;
- separately multiplying n sampled measurements over a period of the second high frequency wave by corresponding sine and cosine values; and separately adding up the sine and cosine products.

* * * * *